(12) United States Patent
LoPresti et al.

(10) Patent No.: US 7,961,327 B1
(45) Date of Patent: Jun. 14, 2011

(54) OPTICAL PH SENSOR

(75) Inventors: Peter LoPresti, Bixby, OK (US); Kerry L. Sublette, Tulsa, OK (US); Kaveh Ashenayi, Tulsa, OK (US); Brian Bovaird, Tulsa, OK (US)

(73) Assignee: Bovaird & Co., Tulsa, OK (US)

( * ) Notice: Subject to any disclaimer, the term of this patent is extended or adjusted under 35 U.S.C. 154(b) by 0 days.

(21) Appl. No.: 12/683,885

(22) Filed: Jan. 7, 2010

Related U.S. Application Data (60) Provisional application No. 61/142,925, filed on Jan. 7, 2009.

(51) Int. Cl.
*G01N 21/00* (2006.01)

(52) U.S. Cl. ........... 356/436; 250/559.11; 250/559.29; 250/227.21; 356/445

(58) Field of Classification Search .......... 356/436–445, 356/36; 250/559.11–559.29, 227.21
See application file for complete search history.

(56) References Cited

U.S. PATENT DOCUMENTS

| | | | |
|---|---|---|---|
| 4,200,110 A | 4/1980 | Peterson et al. | |
| 4,287,427 A | 9/1981 | Scifres | |
| 4,440,022 A | 4/1984 | Masom | |
| 4,624,570 A | 11/1986 | Bertollini | |
| 4,788,444 A | 11/1988 | Williams | |
| 4,871,251 A * | 10/1989 | Preikschat et al. | 356/342 |
| 4,942,306 A | 7/1990 | Colbourne | |
| 5,017,772 A | 5/1991 | Hafle | |
| 5,059,790 A | 10/1991 | Klainer et al. | |
| 5,068,527 A | 11/1991 | Iwamoto et al. | |
| 5,073,027 A | 12/1991 | Krohn et al. | |
| 5,234,835 A | 8/1993 | Nestor et al. | |
| 5,280,548 A | 1/1994 | Atwater et al. | |
| 5,315,672 A | 5/1994 | Padovani | |
| 5,337,376 A | 8/1994 | Ravetti et al. | |
| 5,377,008 A | 12/1994 | Ridgway et al. | |
| 5,408,999 A | 4/1995 | Singh et al. | |
| 5,482,630 A | 1/1996 | Lee et al. | |
| 5,600,433 A | 2/1997 | Buttry et al. | |
| 5,656,241 A | 8/1997 | Seifert et al. | |
| 5,808,730 A | 9/1998 | Danielian et al. | |
| 5,891,747 A | 4/1999 | Farah | |
| 5,900,215 A | 5/1999 | Seifert et al. | |
| 5,995,686 A | 11/1999 | Hamburger et al. | |
| 6,304,328 B1 | 10/2001 | Longtin | |
| 6,356,675 B1 | 3/2002 | Weiss | |
| 6,433,350 B2 | 8/2002 | Hwang et al. | |
| 6,480,638 B1 | 11/2002 | Adkins et al. | |
| 6,559,951 B2 | 5/2003 | Ishikawa et al. | |
| 6,975,388 B2 | 12/2005 | Frot | |
| 7,060,487 B2 | 6/2006 | Lackhart | |
| 7,288,187 B1 | 10/2007 | Bovaird | |
| 7,602,487 B2 * | 10/2009 | Fukami et al. | 356/241.1 |
| 7,628,918 B2 | 12/2009 | Bovaird | |
| 2008/0204708 A1 * | 8/2008 | Shaw | 356/445 |

* cited by examiner

*Primary Examiner* — Gregory J Toatley
*Assistant Examiner* — Iyabo S Alli
(74) *Attorney, Agent, or Firm* — Head, Johnson & Kachigian, P.C.

(57) ABSTRACT

A method to sense pH of a fluid and an optical pH sensor. The method includes the steps of supplying at least a portion of an optical source through an input fiber. The optical source is passed through a sensor head having a sapphire window to a fluid. Optical power reflected from the fluid is collected in a plurality of output fibers in the sensor head. The reflected optical power in the output fibers in the sensor head is thereafter converted to an electrical signal which is used to determine the pH of the fluid.

16 Claims, 9 Drawing Sheets

OPTICAL PH SENSOR

CROSS-REFERENCE TO PENDING APPLICATIONS

This application is based on and claims priority to U.S. Provisional Patent Application Ser. No. 61/142,925, filed Jan. 7, 2009.

BACKGROUND OF THE INVENTION

1. Field of the Invention

The present invention relates to an optical sensor for sensing pH of a fluid and to a method to sense the pH of a fluid. In particular, the present invention relates to a method and apparatus for an optical pH sensor which is used with a system for managing liquidation and degradation of organic waste liquids and solids.

2. Prior Art

Various processes and systems have been employed in the past for the liquidation and degradation of organic waste liquids and solids. These may be found in a variety of containers or vessels, such as a grease trap, an interceptor, pulp and paper mills, wastewater, marine and other waste liquid containers. Ideally, a coordinated treatment of waste is employed including the addition of micro-organisms, enzymes, and/or chemicals, along with oxygen/air to a grease trap or similar waste management apparatus, the monitoring of conditions, and the adjustment to changing conditions in order to optimize the intended liquidation and degradation of the waste.

It is known that maintaining pH levels within certain ranges will optimize the liquidation and degradation of organic waste liquids and solids. Additionally, pH levels outside certain ranges can cause advanced deterioration of gathering systems.

The present invention is intended to operate along with other equipment in a coordinated treatment program including the addition of micro-organisms, enzymes and/or chemicals, along with oxygen/air which is delivered to a vessel or container in order to optimize the intended liquidation and degradation of the waste.

Accordingly, it is a principal object and purpose of the present invention to provide an optical pH sensor which will monitor the pH level of a fluid.

It is an additional object and purpose of the present invention to provide a method to sense the pH level of a fluid using an optical sensor.

It is a further object and purpose of the present invention to provide an optical pH sensor with an ability to prevent fouling of the sensor.

It is a further object and purpose of the present invention to provide an optical pH sensor with an ability to calibrate for identification of problems.

DETAILED DESCRIPTION OF THE PREFERRED EMBODIMENTS

The embodiments discussed herein are merely illustrative of specific manners in which to make and use the invention and are not to be interpreted as limiting the scope of the instant invention.

While the invention has been described with a certain degree of particularity, it is to be noted that many modifications may be made in the details of the invention's construction and the arrangement of its components without departing from the spirit and scope of this disclosure. It is understood that the invention is not limited to the embodiments set forth herein for purposes of exemplification.

Figure 1:
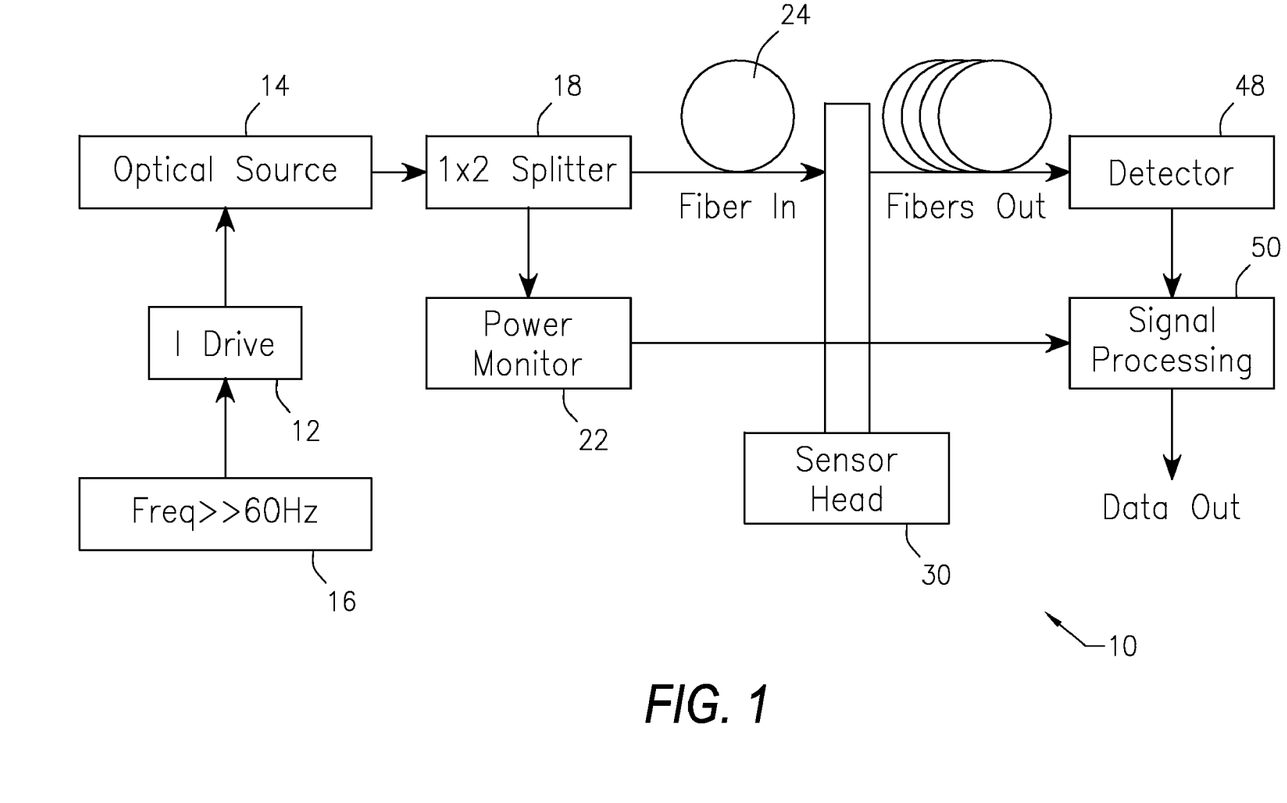
FIG. 1 illustrates a simplified schematic diagram of a system for an optical pH sensor constructed in accordance with the present invention.

FIG. 1 illustrates a simplified schematic diagram of a system 10 which includes an optical sensor of the present invention. An electrical current, as shown in box 12, is delivered to an optical source, such as shown at box 14.

The power to the optical source is modulated by a high frequency, low amplitude alternating current, as shown by box 16. In one embodiment, the optical source modulates at greater than 60 Hertz. The modulation may be of other frequencies within the spirit and scope of the present invention.

The optical source 14 is delivered to a splitter which divides the optical source, such as a 1×2 splitter with a 10/90 (or similar) splitting ratio, as shown at box 18. Thus, a small portion of the optical source is diverted, as shown at box 22, which is utilized to monitor the average power of the light source. The majority of the output from the splitter 18, such as 90% of the optical source, is directed to a large core optic input fiber 24. In one non-limiting example, this may be in the range of 400 to 600 micrometers in diameter. The light source delivered to the emitter or input fiber 24 serves as and becomes the input for the sensor head 30.

Figure 2:
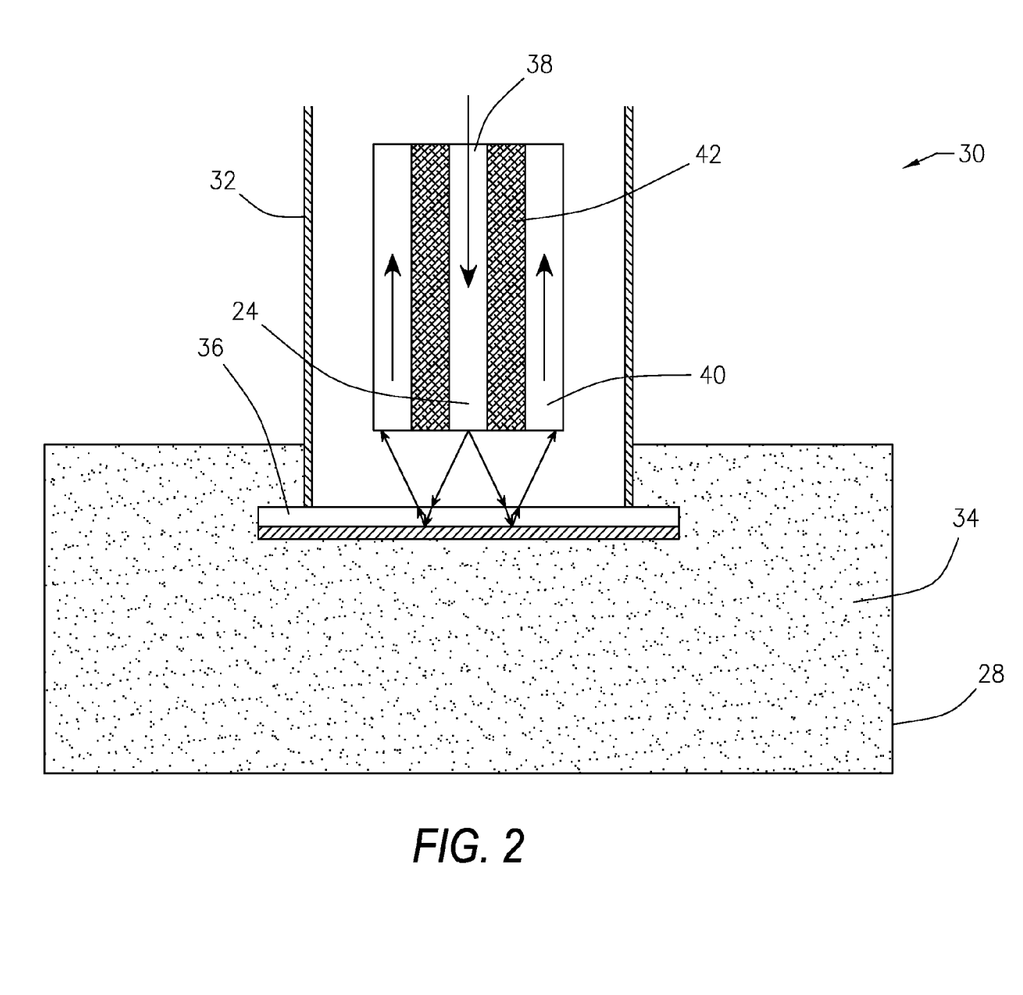
FIG. 2 illustrates a diagrammatic view of the sensor head of the present invention.

The sensor head 30 is shown in detail in the diagrammatic view in FIG. 2. The sensor head 30 is sealed in a tube 32 and is in fluid communication with a fluid 34 in a vessel or container 28. The present invention may be utilized with a wide variety of organic waste liquids and solids.

At the center of the sensor head 30 is the emitter or input fiber 38 which delivers the optical power from the optical source 14. The input fiber 38 brings light to the sensing area from the light source (either a light-emitting diode (LED) or a laser diode (LD)).

The light power passes from the emitter or input fiber 38 through a window 36 that has certain known optical parameters. Man-made or synthetic sapphire is one type of material that may be used for the window 36. A sapphire window 36 is used in the sensor head for two reasons. First, it has a refractive index $n_{sapphire}$ that allows for larger reflections of optical power (compared to standard glass) and sets the operating point in a more sensitive part of the equation for r the reflectivity of the boundary between the window 36 and the fluid 34. Stated in other words, the changes in r (and hence $R=r^2$) that occurs due to a change in $n_{fluid}$ is greater for refractive index of sapphire (which is 1.7) than it is for the refractive index of standard glasses (which are around 1.5). Second, the sapphire window is much more resistant to scratching and other damage. This means that the optical properties of the window will be preserved for far longer than would those of standard glass. Therefore, the sensor's life cycle will be longer.

Figure 4:
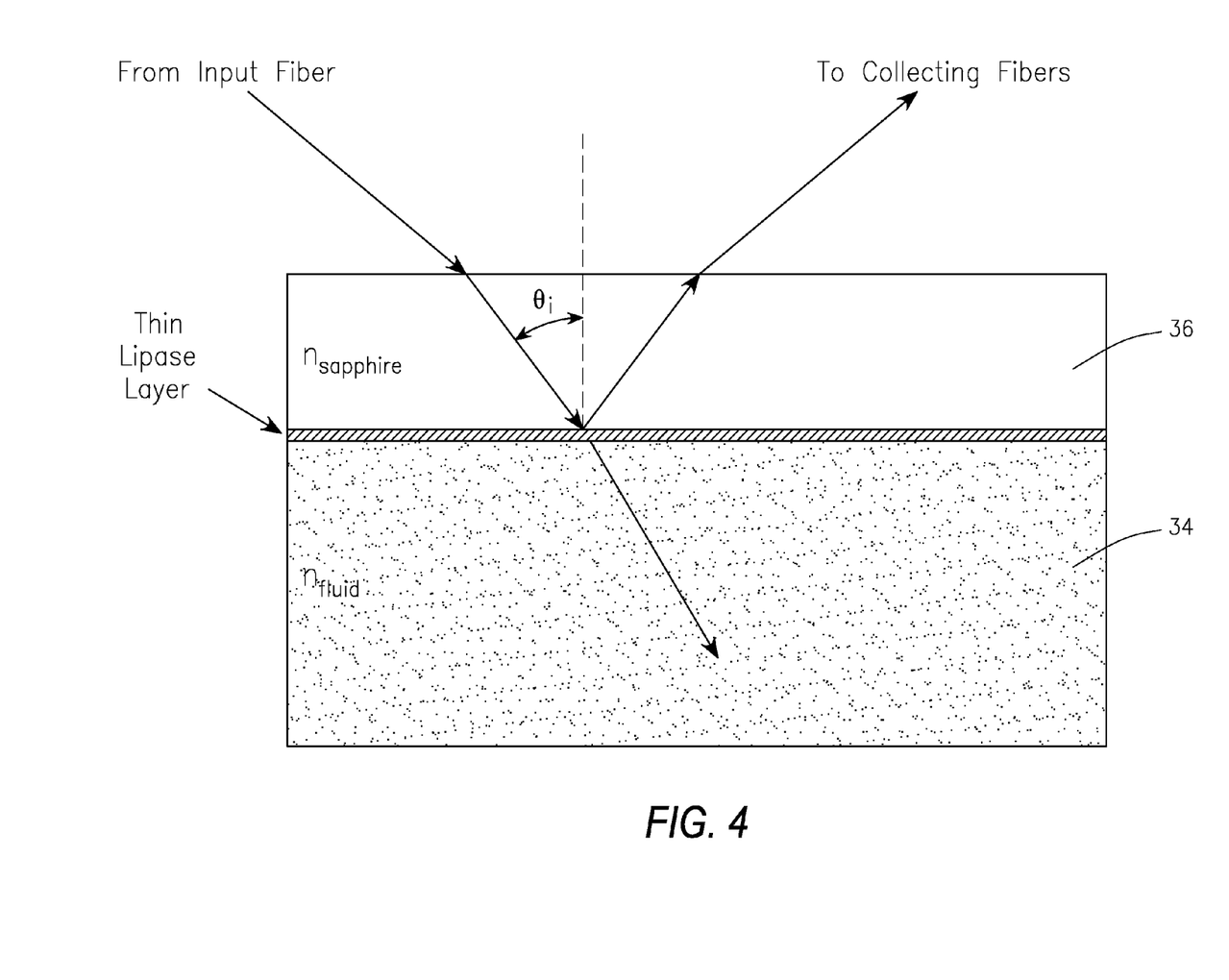
FIG. 4 illustrates a diagrammatic view of an optical power input to the sensor head and an output reflected from the sensor head.

The light is emitted from the end of the input fiber 38 at a broad angle range and is permitted to strike the sapphire window 36. The light enters and passes through the sapphire window and is then reflected at the boundary between the window and the fluid 34 to be sensed. The reflected light power is a function of the reflectivity at the boundary. It is known that light spreads out as it leaves the input fiber. This spreading causes the light rays to enter the sapphire window at many different angles. The light enters the sapphire and then contacts the boundary between the sapphire and the fluid 34. Each ray in the sapphire contacts the boundary at an angle $\theta_i$. As best seen in FIG. 4, some of the power in the input light is reflected by the boundary, and the rest is transmitted. The percentage of the optical power that is reflected is a function of the ratio of the refractive index of the sapphire ($n_{sapphire}$) and the refractive index of the fluid ($n_{fluid}$), as indicated in the following equations.

$$n = \frac{n_{fluid}}{n_{sapphire}}$$

$$r = \frac{\cos\theta_i - \sqrt{n^2 - \sin^2(\theta_i)}}{\cos\theta_i + \sqrt{n^2 - \sin^2(\theta_i)}}$$

$$R = \frac{\text{power reflected}}{\text{input power}} = r^2$$

A lipase layer will be very, very thin so that it does not significantly impact the optical properties and behaviors at the boundary between the sapphire and the fluid being tested. On the external side of the sapphire window 36, a protein coating may be utilized to prevent fouling of the window by fat, oil and grease in the fluid 34. If the protein coating is sufficiently thin, it will only mildly alter the properties of the window and fluid interface. The protein layer or lipase layer on the signal head will prevent build up on the sensor.

Returning to a consideration of FIG. 2, the light reflected from the fluid is collected by plurality of receiver or output fibers 40 in the sensor head which surround the input fiber 34. A plurality of spacers 42 may be arranged surrounding the input fiber 34 and juxtaposed between the input fiber 34 and the output fibers 40.

Figure 3:
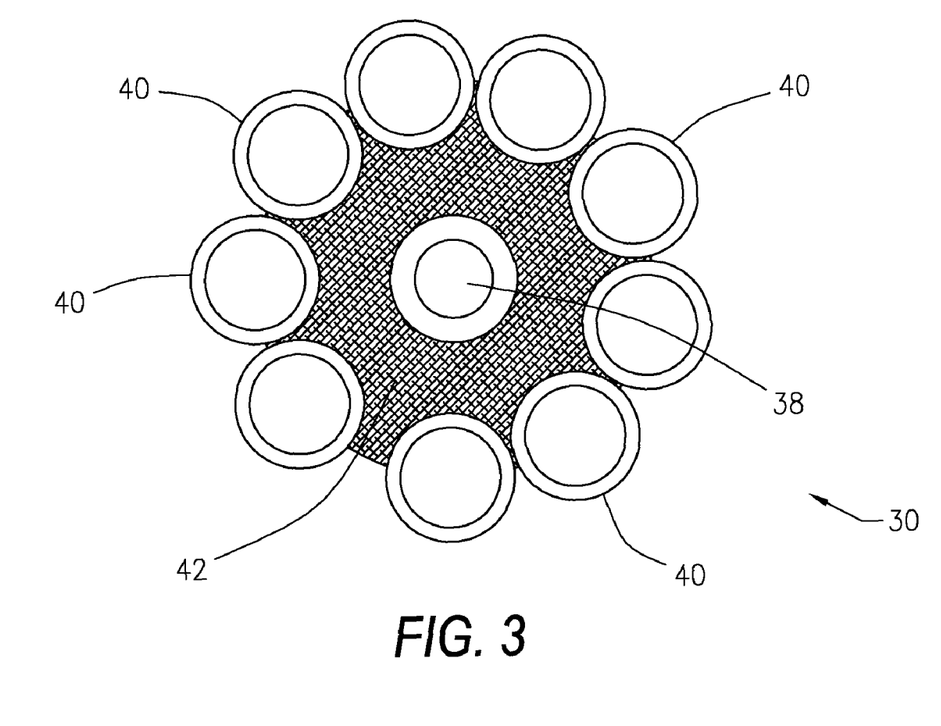
FIG. 3 illustrates a partial sectional view of the sensor head shown in FIG. 2.

The reflected power is collected by the output or collecting fibers that surround the input fiber and form the outer ring of the fiber bundle, as shown in FIG. 3. In an ideal case, none of the optical power that is transmitted into the fluid gets back to the collecting fibers. As measured in the laboratory, the quantity $n_{fluid}$ is a function of the pH of the fluid from the container. As the pH of the fluid changes, this will cause a change in $n_{fluid}$ and there will subsequently be a change in the value of the reflected power. As the refractive index of the fluid ($n_{fluid}$) decreases, the reflected power increases. Conversely, as the refractive index of the fluid ($n_{fluid}$) increases, the reflected power decreases.

The amount of power reflected is also a function of the angle $\theta_i$ of the incoming light. A change in $n_{fluid}$ will produce a larger change in the reflected power as the angle $\theta_i$ becomes larger. This will allow the sensor head to be more sensitive to changes in $n_{fluid}$ and hence to changes in pH. The spacers used in the fiber bundle force the collecting fibers to only collect light rays that started at larger values of $\theta_i$, thus increasing sensitivity. It should be noted that the maximum value of R is one, equivalent to 100% reflection.

As seen in FIG. 3, the diameters of the core(s) of the collecting fibers are different than the core or cores for the input fiber. The cores of the collecting fibers are larger (typically 800 to 1000 μm) than the core(s) of the input fiber (typically 400 to 600 μm). The cores of the collecting fibers are larger so that they can collect rays with a wide range of angles $\theta_i$ and therefore improve both the amount of reflected light that is collected and the observable change in the reflected light caused by the change in pH.

The sapphire window 36 may be coated with a thin protein layer, such as a lipase layer. The purpose of the lipase layer is to prevent fouling of the sapphire window 36 by the fat, oil and grease present in the container, such as in a grease trap. The lipase layer interacts with and repels the fat, oil and grease, preventing these compounds from sticking to the surface of the window 36. As long as the lipase layer is in good working order, the sensor 30 should function as designed. If the lipase layer begins to fail, the characteristics of the sensor will quickly change, most likely causing the reflected power to increase rapidly towards 100% of the input power. This change would easily be noticed by the sensor's analyzing software, and the software could signal the need for a cleaning of the window and reapplication of the lipase layer.

The input signal for the sensor head 30 is provided by a modulated optical source. The optical source can be either a laser diode (LD) or a light-emitting diode (LED). The wavelength of the source is one that is not absorbed strongly by the fluid under test. Typically this will be in the visible spectrum range, from blue (a wavelength of 480 nanometers (nm)) to the lower part of the red region (600-630 nm) for most water-based fluids, since water begins to absorb strongly in the infrared region (>680 nm).

For either optical source, the output power of the source is controlled by an input current signal. This signal has two parts. The first part is constant with time, and this is referred to as the D.C. or bias current. The D.C. current value is set to determine the base level of optical power emitted by the source. The second part of the current signal is a periodic modulation with time, typically in the form of a sine function or a square-wave function. This part is called the a.c. or modulation current. This modulation current alternately adds to or subtracts from the bias current, causing the optical power of the source to increase and then decrease repeatedly at a desired repetition rate (i.e. frequency). The amplitude of the modulation current is chosen to create changes In optical power that are easily detected at the output of the sensor system without overloading that system. The frequency is typically chosen at least 2 times bigger than 60 Hertz to minimize interference from external power sources.

The optical power emitted by the source is split into two components. For example, a 1-input, 2-output (1 by 2) power splitter directs >95% of the source light to the sensor head, and <5% of the source light to a power monitoring circuit. The power monitoring circuit consists of a photodetection device (such as a photodiode or phototransistor) and attendant circuitry that converts the incoming light into an electrical signal proportional to the incoming optical power. This signal is used by the signal processing portion of the system to compensate for changes in the D.C. value of the optical power emitted by the source, which can change due to aging, environmental damage, or unplanned changes in the bias current. The other 95% of the source light is used for measurement purposes in the sensor head.

In one non-limiting embodiment, as shown in FIG. 3, nine output fibers 40 are arranged circumferentially around the input fiber. The fiber bundle is used to collect the maximum reflected light signal and translate the light signal to a detector. The output fibers are larger core fibers ranging between 600 micrometers and 1 millimeter in diameter to collect multiple angles and enhance sensitivity. The output signal collected from the output fibers 40 is delivered to a commercially available photo optical detector which is capable of translating a light signal to an electrical signal.

Accordingly, the sensor head 30 will sense the optical density of the fluid 34 in the container.

Figure 5:
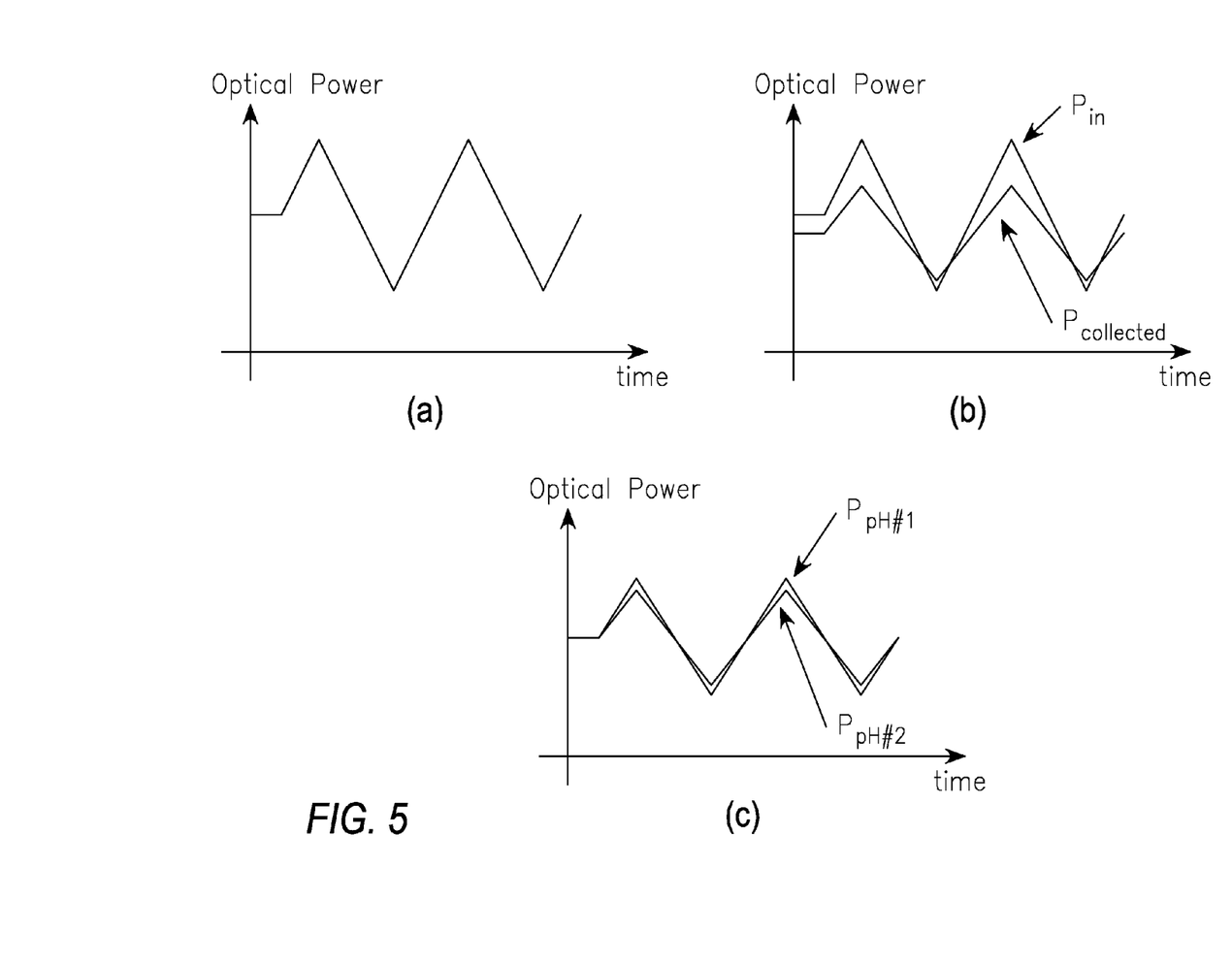
FIG. 5 illustrates a series of graphs charting optical power against time.

When the optical power enters the input fiber Of the sensor head, the power as a function of time might look like the signal shown in FIG. 5(a). The modulating current has been depicted as a triangle wave to make the picture easier to draw.

According to the description and equations above, a fraction of this light, given by R times $P_{in}$ (the input power) is reflected from the boundary between the sapphire and the fluid, and this reflected power is then collected by the collecting fibers. The original signal plus the reflected signal are shown in FIG. 5(b). Notice that the two signals have different amplitude, where amplitude is defined as the distance between the lowest and highest part of the signal. The reflected signal will always have a smaller amplitude than the input signal under normal operating conditions for the sensor. The change in the amplitude is proportional to R, which is dependent on $n_{fluid}$, which is dependent on the pH of the fluid. Fluids with different pH values will have different values of $n_{fluid}$ and thus R. Therefore, fluids with different pH values will result in different amplitudes of $P_{collected}$, as shown in FIG. 5(c). The amplitude value can be converted back into a pH value in the signal processing software component of the system.

The optical power carried away from the sensor head 30 by the collecting fibers is brought to the receiver unit where it is converted to electrical voltage and then processed. The first stage of this process consists of bringing the opposite ends of the collecting fibers (the ends not in the sensor) to a photodetection device or detector 48. As noted previously, the photodetection device 48, combined with electrical circuitry, converts the optical power signal into an electrical signal. In a single conversion system, the electrical voltage signal is proportional to the optical power signal. A filter circuit, placed after the detector, may be employed to block signals that are not directly related to the sensor signal. For example, if a sine wave modulation is used on the optical source at 300 Hertz frequency, a device called a band-pass filter could be employed that blocked signals at most frequencies and let through signals in a small range of frequencies (+ or − 10 Hz for example) around 300 Hertz. This would improve the quality of the voltage signal obtained from the detector by reducing the noise in the signal. The filter can be built using electronic components or it can be implemented in software as part of the signal processing program.

The signal processing system then takes the electronic signal from the detector 48 and the signal from the power monitoring system 22 and determines the pH of the fluid under test. The basic steps of the signal processing system are as follows:

(1) The input signal from the detector 48 is adjusted to compensate for variations in the optical power of the source. The signal from the power monitoring system is converted into a number that represents the current D.C. (average) power of the optical source. The signal from the sensor is then divided by this number, resulting in a ratiometric signal. If the sensor is working correctly, a 1% decrease in the optical power of the source should produce a proportional decrease in the signal power received from the collecting fibers. The ratio of the signal power to the source power should therefore remain constant. Additional processing is needed for larger changes in optical power as the sensor does not remain linear in that case. Any additional filtering or averaging used to adjust or "clean" the signal would be performed at this time.

(2) Abnormal behavior from the sensor is checked, and reaction taken as necessary. Abnormal behavior may result from (a) particles near the sapphire window that temporarily increase the reflection independent of the refractive index of the fluid, (b) coating of the sapphire window by fat, oil and grease, or (c) failure of one or more components. The signal processing software would calculate the pH and would go through a series of checks in an attempt to identify the problem, and wait a pre-determined length of time to see if the problem clears. If the problem does not clear, the sensor will need cleaning or maintenance.

(3) The ratiometric reading is adjusted for temperature of the system. A separate temperature sensor (not shown) may be employed to obtain the fluid temperature over time. Prior calibration and measurement will produce a formula stored in memory for correcting the reading from the sensor.

(4) The pH of the fluid is computed. Reversing the formulas given above, the pH of the fluid be computed from knowledge of the physical design of the sensor (which determines the angle $\theta_i$) and the corrected ratiometric signal computed previously.

Once all of these steps are completed, the system will produce a reading for the pH of the fluid under test.

Figure 6:
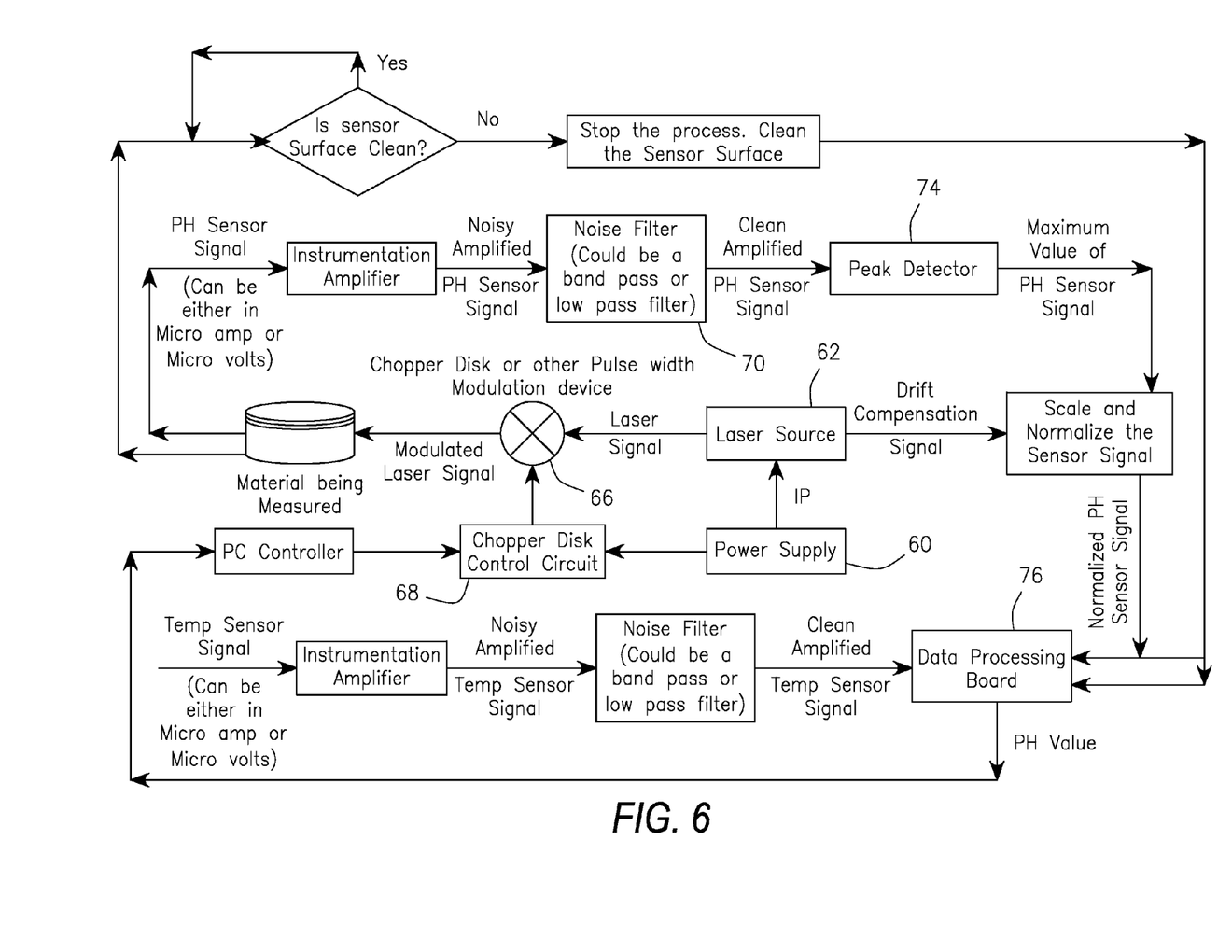
FIGS. 6 and 7 illustrate diagrammatic flow charts of the process to calculate pH in accordance with the present invention.
Figure 7:
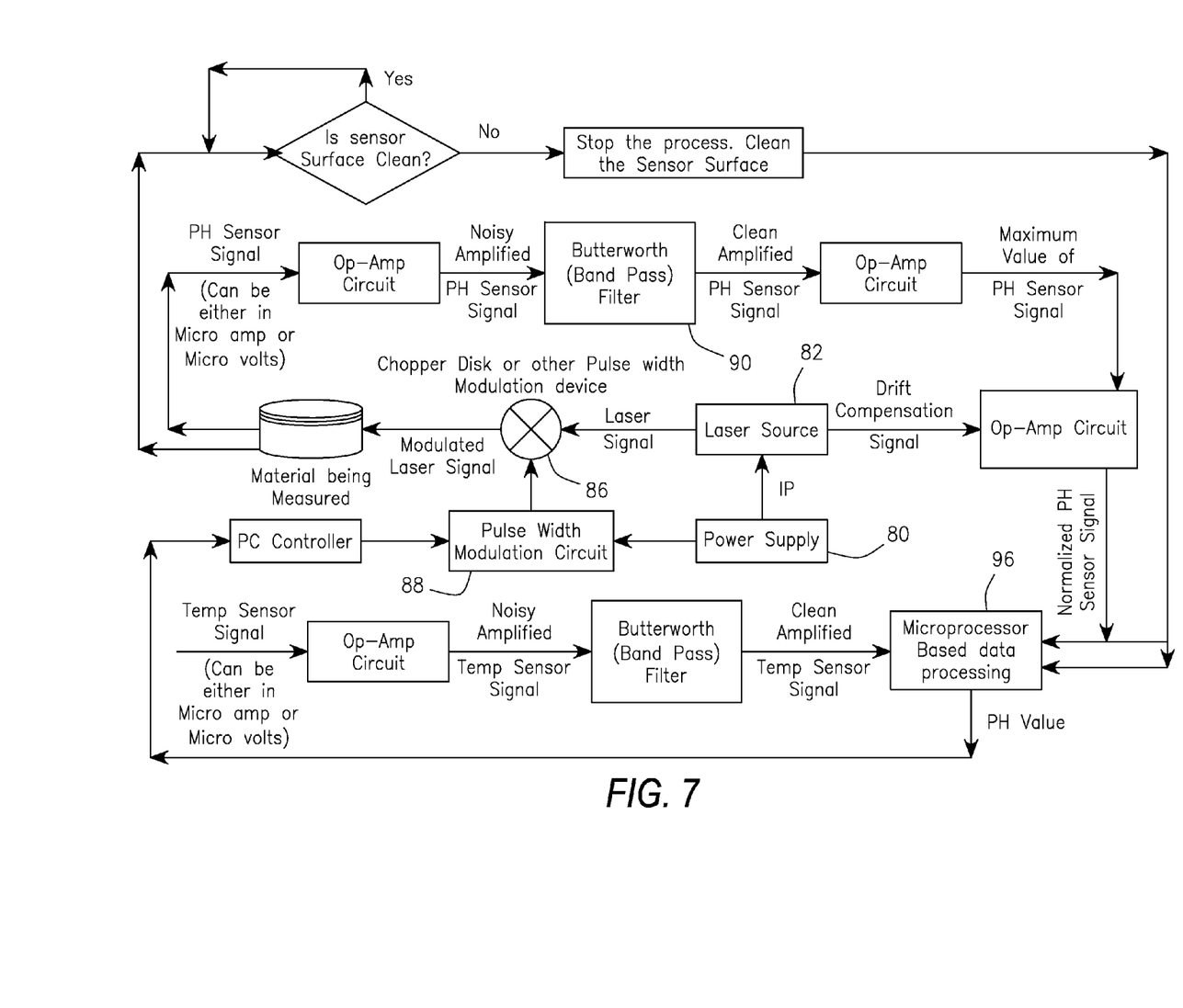

FIGS. 6 and 7 show diagrammatic flow charts of the operation of the system to determine and calculate a pH value.

With reference to FIG. 6, the sensor system is composed of several elements, in addition to the sensor head, each critical to the proper measurement of the pH of a fluid material under investigation. These are (a) generation of the interrogating signal, (b) sensor signal processing, (c) signal normalization and modification, (d) pH calculation, and (e) detection of sensor fouling. Each of these parts is described in what follows. Note that, while one combination of source and detection systems is indicated in the drawing, two such systems— operating in parallel at different wavelengths—may be required in some cases to uniquely determine the pH of the material under test.

A. Generation of the Interrogating Signal

A power supply 60 provides electrical power to a laser source 62 and the circuit that controls modulation of the laser output. The power supply provides a stable current to the laser source, thereby setting directly the output optical power from the laser, as determined by the current-power curve of the laser. A small fraction of the optical power emitted by the laser is split off from the main signal (either using a power splitter at the laser output or by taking optical power from the rear mirror of the laser) and this power is collected by a sensing photodetector. The sensing photodetector converts the optical power into an electrical signal (called the Drift Compensation Signal) that is used by the signal normalization and modification part of the system and can also be used to provide a feedback path for further stabilizing the output power of the laser (this latter use is not shown in the diagram). The laser runs in continuous wave (cw) mode, so that the output power of the laser is of constant value. The optical power is passed through a device 66 that modulates the amplitude of the optical signal. This device may be a shutter that periodically blocks and lets pass the laser light (for example, a chopping disc or acousto-optic modulator) or may be an electro-optic modulator that blocks and lets pass the light by means of controlled interference (such as a Mach-Zender interferometer). The frequency of the modulation and the durations for which the light is blocked and let past is determined by a PC controller and implemented by the Pulse Width Modulation Control Circuit (labeled Chopper Disk Control Circuit 68 in this diagram). Alternatively, the modulation of the optical power may be implemented by directly modulating the current supplied to the source 62, wherein the power supply 60 is directly controlled by the Pulse Width Modulation Control Circuit 68. The modulated signal is then sent to the sensor head via optical fiber.

B. Sensor Signal Processing

The signal from the sensor is a pulse-width modulated signal that can be either a voltage signal or a current signal. The signal is small—on the order of a few tens of microvolts or microamps—and contains a random noise component due to environmental interference with the electronics and from within the laser source. An instrumentation amplifier selectively amplifies the pulse-width modulated signal while providing little or no gain to the electrical noise component. The noisy, amplified signal is then passed to a noise filter circuit. This circuit passes frequency components that are specific to the pulse-width modulation signal, and blocks other frequency components, thereby reducing significantly the noise component of the sensor signal. A band pass filter 70, designed to pass the first several harmonics of the pulse-width modulated signal, provides the best performance. A low pass filter provides adequate performance if the frequency of the pulse-width modulation signal is kept low and the interfering noise is of high-frequency composition in comparison. A peak detector 74 then measures the maximum value (and minimum value if this value is not originally zero) of the signal that exits the noise filter. This maximum value is the raw pH sensor Signal.

C. Signal Normalization and Modification

Signal normalization is performed using the raw pH sensor signal and the Drift Compensation Signal. Dividing the sensor signal by the Drift Compensation Signal normalizes the raw pH sensor signal. The resulting ratio is then scaled according to the maximum expected normalized signal produced by the sensor. This maximum signal occurs when the sensor head is surrounded only by air, and this maximum signal is measured by the system prior to insertion of the sensor head into the material being measured.

Signal modification is facilitated by obtaining a measurement of the temperature of the material under test using a physically distinct temperature sensor. The signal from the temperature sensor is similar in size and format to the pH sensor signal, and is processed using the signal-processing scheme described above. The temperature signal is used to adjust the pH sensor signal reading to account for the temperature dependence of the material under test's refractive index, which alters slightly the reading from the pH sensor as the material's temperature varies.

D. pH Calculation

A microprocessor 76 uses the inputs from the Signal Normalization and Modification system to calculate the pH of the material under test. The microprocessor 76 contains within its memory a calibration curve that relates the modified normalized signal to the pH of the material under test. This calibration curve is presumed calculated with a sample of the material prior to installation of the sensor. The microprocessor takes the input value of the normalized and scaled sensor signal, adjusts the signal according to the reading from the temperature sensor, and then applies the calibration curve to calculate the pH. The pH value is the primary output of the sensor system.

An additional function of the microprocessor 76 is to provide feedback control to the Generation of the interrogating Signal system. If the input signal from the pH sensor is of insufficient amplitude to make a reliable reading, the microprocessor can provide information to the unit that controls the modulating block. This allows adjustment of the frequency and amplitude of the modulation to improve signal quality.

E. Detection of Sensor Fouling

It is expected that the sensor head will periodically foul due to the operating environment, either through deterioration of the lipase coating or particulates sticking to the window. In each of these cases, the reflectivity of the sensor head will be greatly increased, and thus the optical signal from the sensor and the subsequent electrical signal from the Sensor Signal Processing system will become quite large. In the most likely case, the sensor signal will exceed that obtained when the sensor is in air, which is the largest expected signal if the sensor is not fouled. Therefore, the microprocessor and/or the Signal Normalization and Modification block interprets a reading above this value as a clear indication that the sensor is fouled. The second likely case is that the signal is below the value expected for operation in air, but is outside the expected range of operation, as determined by the calibration curve, even after scaling, normalization, and temperature adjustments are applied. In this case only the microprocessor block is able to interpret correctly that the sensor is fouled.

When the sensor is considered fouled by the microprocessor or the Signal Normalization and Modification block, the sensor is retracted from the material under test. A motor or similar mechanical device lifts the sensor head from the material and moves it to a separate chamber for cleaning and reapplication of the lipase coating. The microprocessor evaluates the sensor signal after this process to (a) verify that the sensor is again operating properly and (b) make minor adjustments or modifications to the pH calculation process to account for small discrepancies that may result from differences between the new lipase coating and the previous lipase coating. The sensor head is then returned to the primary chamber and lowered back into the material under test to continue normal operation.

FIG. 7 illustrates a diagrammatic flow chart of an alternate process to determine pH. The sensor system is composed of several elements, in addition to the sensor head, each critical to the proper measurement of the pH of a material under investigation. These are (a) generation of the interrogating signal, (b) sensor signal processing, (c) signal normalization and modification, (d) pH calculation, and (e) detection of sensor fouling. Each of these parts is described in what follows. Note that, while one combination of source and detection systems is indicated in the drawing, two such systems—operating in parallel at different wavelengths—may be required in some cases to uniquely determine the pH of the fluid material under test.

A. Generation of the Interrogating Signal

A power supply 80 provides electrical power to a laser source 82 and the circuit that controls modulation of the laser output. The power supply provides a stable current to the laser source, thereby setting directly the output optical power from the laser, as determined by the current-power curve of the laser. A small fraction of the optical power emitted by the laser is split off from the main signal (either using a power splitter at the laser output or by taking optical power from the rear mirror of the laser) and this power is collected by a sensing photodetector. The sensing photodetector converts the optical power into an electrical signal (called the Drift Compensation Signal) that is used by the signal normalization and modification part of the system and can also be used to provide a feedback path for further stabilizing the output power of the laser (this latter use is not shown in the diagram). The laser runs in continuous wave (cw) mode, so that the output power of the laser is of constant value. The optical power is passed through a device 86 that modulates the amplitude of the optical signal. This device may be a shutter that periodically blocks and lets pass the laser light (for example, a chopping disc or acousto-optic modulator) or may be an electro-optic modulator that blocks and lets pass the light by means of controlled interference (such as a Mach-Zender interferometer). The frequency of the modulation and the durations for which the light is blocked and let past is determined by a PC controller and implemented by the Pulse Width Modulation Control Circuit 88. Alternatively, the modulation of the optical power may be implemented by directly modulating the current supplied to the source 82, wherein the power supply 80 is directly controlled by the Pulse Width Modulation Control Circuit 88. The modulated signal is then sent to the sensor head via optical fiber.

B. Sensor Signal Processing

The signal from the sensor is a pulse-width modulated signal that can be either a voltage signal or a current signal. The signal is small—on the order of a few tens of microvolts or microamps—and contains a random noise component due to environmental interference with the electronics and from within the laser source. An instrumentation amplifier selectively amplifies the pulse-width modulated signal while providing little or no gain to the electrical noise component. This amplifier is readily constructed using one of several operational amplifier (op-amp) based circuits. The noisy, amplified signal is then passed to a noise filter circuit. This circuit passes frequency components that are specific to the pulse-width modulation signal, and blocks other frequency components, thereby reducing significantly the noise component of the sensor signal. A band pass filter 90, designed to pass the first several harmonics of the pulse-width modulated signal, provides the best performance. A Butterworth filter constructed with active components provides flatness in the passband that is needed to accurately interpret the small changes in the signal resulting from changes in pH, and provides additional signal gain. A low pass filter provides adequate performance if the frequency of the pulse-width modulation signal is kept low and the interfering noise is of high-frequency composition in comparison. A peak detector, constructed from operational amplifiers and diode circuits, then measures the maximum value (and minimum value if this value is not originally zero) of the signal that exits the noise filter. This maximum value is the raw pH sensor signal.

C. Signal Normalization and Modification

Signal normalization is performed using the raw pH sensor signal and the Drift Compensation Signal. Dividing the sensor signal by the Drift Compensation Signal normalizes the raw pH sensor signal. The resulting ratio is then scaled according to the maximum expected normalized signal produced by the sensor. This maximum signal occurs when the sensor head is surrounded only by air, and this maximum signal is measured by the system prior to insertion of the sensor head into the material being measured. Scaling and normalization is performed with standard operational amplifier circuits, with the scaling circuits using an adjustable bias scheme that is set during initial calibration and subsequently adjusted as needed by the microprocessor or service personnel to maintain accuracy over time.

Signal modification is facilitated by obtaining a measurement of the temperature of the material under test using a physically distinct temperature sensor. The signal from the temperature sensor is similar in size and format to the pH sensor signal, and is processed using the signal-processing scheme described above. The temperature signal is used to adjust the pH sensor signal reading to account for the temperature dependence of the material under test's refractive index, which alters slightly the reading from the pH sensor as the material's temperature varies.

D. pH Calculation

A microprocessor 96 uses the inputs from the Signal Normalization and Modification system to calculate the pH of the material under test. The microprocessor contains within its memory a calibration curve that relates the modified normalized signal to the pH of the material under test. This calibration curve is presumed calculated with a sample of the material prior to installation of the sensor. The microprocessor takes the input value of the normalized and scaled sensor signal, adjusts the signal according to the reading from the temperature sensor, and then applies the calibration curve to calculate the pH. The pH value is the primary output of the sensor system.

An additional function of the microprocessor is to provide feedback control to the Generation of the Interrogating Signal system. If the input signal from the pH sensor is of insufficient amplitude to make a reliable reading, the microprocessor can provide information to the unit that controls the modulating block. This allows adjustment of the frequency and amplitude of the modulation to improve signal quality.

E. Detection of Sensor Fouling

It is expected that the sensor head will periodically foul due to the operating environment, either through deterioration of the lipase coating or particulates sticking to the window. In each of these cases, the reflectivity of the sensor head will be greatly increased, and thus the optical signal from the sensor and the subsequent electrical signal from the Sensor Signal Processing system will become quite large. In the most likely case, the sensor signal will exceed that obtained when the sensor is in air, which is the largest expected signal if the sensor is not fouled. Therefore, the microprocessor and/or the Signal Normalization and Modification block interprets a reading above this value as a clear indication that the sensor is fouled. The second likely case is that the signal is below the value expected for operation in air, but is outside the expected range of operation, as determined by the calibration curve, even after scaling, normalization, and temperature adjustments are applied. In this case only the microprocessor block is able to interpret correctly that the sensor is fouled.

When the sensor is considered fouled by the microprocessor or the Signal Normalization and Modification block, the sensor is retracted from the material under test. A motor or similar mechanical device lifts the sensor head from the material and moves it to a separate chamber for cleaning and reapplication of the lipase coating. The microprocessor evaluates the sensor signal after this process to (a) verify that the sensor is again operating properly and (b) make minor adjustments or modifications to the pH calculation process to account for small discrepancies that may result from differences between the new lipase coating and the previous lipase coating. The sensor head is then returned to the primary chamber and lowered back into the material under test to continue normal operation.

The present invention was tested in various ways.

Figure 8:
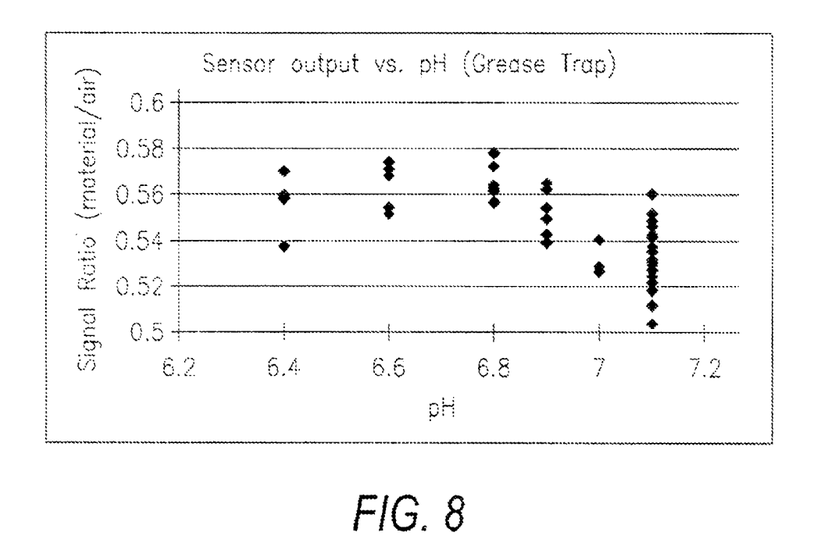
FIG. 8 is a chart showing sensor head response as a function of pH.

FIG. 8 shows the sensor head response as a function of pH for samples collected from an operating grease trap over a 6-hour span. The output of a laser operating at 633 nm was modulated by imposing a sine wave modulation on the laser's drive current at a frequency of 1 kHz. The output signal from the sensor head was input to an oscilloscope. The DC component of the signal was removed and the resultant a.c. signal was averaged using a 256-sweep running average. The peak-to-peak value of the signal was measured using the measurement functions available on the oscilloscope.

In order to minimize the effects of variations in the laser output power with time, the sensor output was first measured while the sensor was suspended in air. This provided a normalization reading for the sensor output. The sensor was then lowered into the material sample, taking care to maintain the same orientation of the sensor with respect to the container and the same depth of the sensor window with respect to the surface of the sample. Readings in both cases were recorded over 30 seconds of operation. The sensor was raised out of the sample, extra fluid wicked off of the window, and the process repeated a minimum of three times for each sample on each day of testing. The data from each combination of air and material measurements were averaged over the 30-second time frame and then the material measurement was divided by the air measurement to produce the signal ratio reported in the graph.

Figure 9:
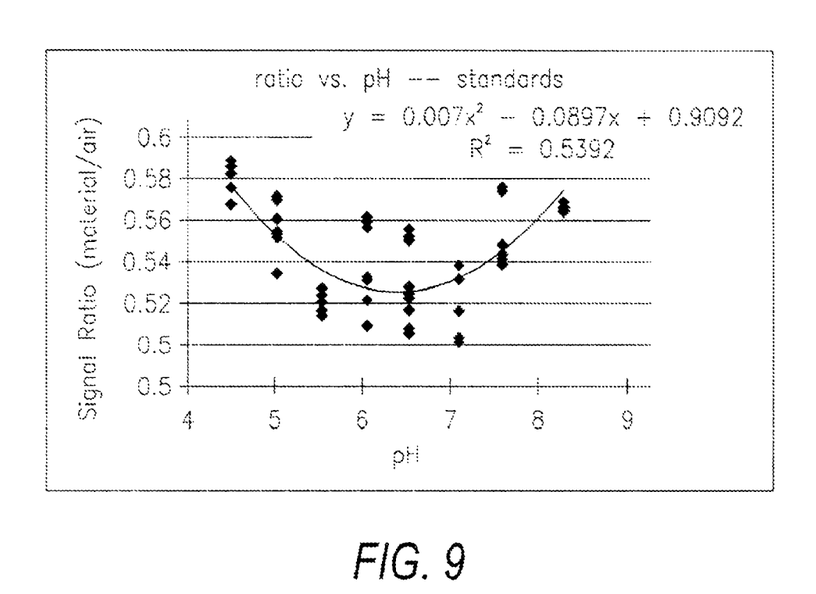
FIG. 9 is a chart showing sensor head response as a function of pH.

FIG. 9 shows sensor head response as a function of pH for pH buffer solutions ranging from 4.5 to 8.2. The output of a laser operating at 633 nm was modulated by imposing a sine wave modulation on the laser's drive current at a frequency of 1 kHz. The output signal front the sensor head was input to an oscilloscope. The DC component of the signal was removed and the resultant a.c. signal was averaged using a 256-sweep running average. The peak-to-peak value of the signal was measured using the measurement functions available on the oscilloscope.

In order to minimize the effects of variations in the laser output power with time, the sensor output was first measured while the sensor was suspended in air. This provided a normalization reading for the sensor output. The sensor was then lowered into the material sample, taking care to maintain the same orientation of the sensor with respect to the container and the same depth of the sensor window with respect to the surface of the sample. Readings in both cases were recorded over 30 seconds of operation. The sensor was raised out of the sample, extra fluid wicked off of the window, and the process repeated a minimum of three times for each sample on each day of testing. The data from each combination of air and material measurements were averaged over the 30-second time frame and then the material measurement was divided by the air measurement to produce the signal ratio reported in the graph.

Figure 10:
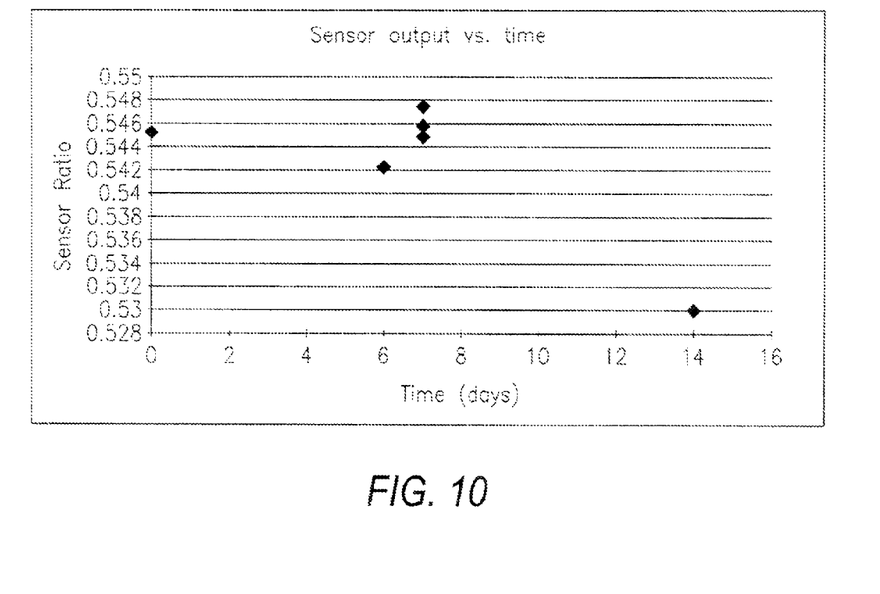
FIG. 10 is a chart showing output of the sensor over time.

FIG. 10 is a graph showing the results of the time dependent test of the sensor, embedded in a grease trap sample over a period of two weeks. The sample was the one taken at 6:30 pm, and had an initial pH of 7.0. For the first 7 days, no notable change in the sensor operation was noted. At 14 days, the sample had lost 3 mm of height in a container with diameter of 1.5 inches (about 38.1 mm), which would be sufficient fluid loss to alter the pH of the sample. The sensor reading dropped by about 0.015, which corresponds to a 0.1 increase in pH according to the prior measurements on the grease trap samples.

In summary, the present invention provides an optical sensor for sensing pH of a fluid utilizing an optical light source biased with direct current with temperature and power controls. The power is modulated by a relatively high frequency, low amplitude alternating current superposed on the direct current. The optical light source is split with a small portion used to monitor average power and a large portion used as input to a sensor head. A fiber bundle in the sensor heart collects the maximum reflected signal and is converted to an electrical signal, which is used to determine pH.

Whereas, the present invention has been described in relation to the drawings attached hereto, it should be understood that other and further modifications, apart from those shown or suggested herein, may be made within the spirit and scope of this invention.

What is claimed is:

1. A method to sense pH of a fluid, said method comprising the steps of:
supplying an optical source through an input fiber;
passing said optical source at a range of predetermined input angles to a sensor head having a transparent window in contact with a fluid, wherein said window has a high refractive index, and wherein a side of said window in contact with said fluid is coated with a thin protein layer to prevent fouling of said window due to accumulation of fat, oil and/or grease within said fluid on said window;
forming a reflective boundary between said fluid and said side of said window in contact with said fluid,
collecting optical power reflected from said reflective boundary between said window and said fluid by a plurality of output fibers in said sensor head, wherein said output fibers are positioned with respect to said input fiber so as to collect optical power reflected from said reflective boundary at predetermined output angles; and
detecting a fouling of said sensor head based on reflected optical power collected by said output fibers;
if no fouling of said sensor head is detected, converting said reflected optical power collected by said output fibers to pH of said fluid.

2. A method as set forth in claim 1 wherein said step of supplying said optical source further comprises the step of periodically modulating said optical source from a light emitting diode with time in a sinusoidal manner around an average output value.

3. A method as set forth in claim 1 wherein said step of supplying said optical source further includes periodically modulating said optical source from a laser diode with a continuous tone around an average output value.

4. A method as set forth in claim 1 wherein said sensor head includes said input fiber centrally located surrounded by said plurality of said output fibers, and wherein said sensor head is constructed such that collecting said reflected optical power by said output fibers is dependent upon said reflected optical power reflected at said reflective boundary from said optical source supplied by said input fiber.

5. A method as set forth in claim 4 wherein said plurality of output fibers each have diameters larger than said input fiber.

6. A method as set forth in claim 1 including the additional step of splitting said optical source prior to delivery to said input fiber so that a small portion of said optical source is directed to a power monitoring circuit.

7. A method as set forth in claim 6 including the additional steps of dividing said reflected optical power by power from said power monitoring circuit to produce a ratiometric signal, and adjusting said ratiometric signal for temperatures of said fluid.

8. A method as set forth in claim 1 wherein said step of detecting a fouling of said sensor head based on said reflected optical power in said output fibers further comprises the steps of:
if said reflective optical power is above a predetermined expected upper reading, servicing said sensor head; and if said reflective optical power is below a predetermined expected lower reading, servicing said sensor head.

9. A method as set forth in claim 1 wherein said step of converting said reflected optical power in said output fibers to pH of said fluid is accomplished with signal processing software.

10. An optical pH sensor which comprises:
an input fiber supplied with an optical source;
a sensor head in communication with said optical source;
a transparent window in said sensor head to permit passage of said optical source from said input fiber at a plurality of predetermined range of angles to a fluid to be tested, and said window constructed of a material having a high refractive index;
a thin protein layer coating an external surface of said window between said window and said fluid to be tested, and said thin protein layer constructed to prevent fouling of said window due to accumulation of fat, oil and/or grease within said fluid on said window;
a plurality of output fibers in said sensor head for collecting optical power reflected from a reflective boundary between said window and said fluid, said output fibers constructed in said sensor head with respect to said input fiber to collect optical power reflected from said reflective boundary at predetermined output angles, and said input fiber of said sensor head centrally located surrounded by said plurality of said output fibers;
a receiver unit for converting optical output power to electrical voltage in order to determine pH of said fluid; and
a sensor fouling detection and servicing unit for determining fouling of said sensor head due to accumulation of fat, oil and/or grease within said fluid on said window of said sensor head and/or deterioration of said thin protein layer.

11. An optical pH sensor as set forth in claim 10 wherein said optical source emanates from a light emitting diode which is periodically modulated with time in a sinusoidal manner around an average output value.

12. An optical pH sensor as set forth in claim 10 wherein said optical source emanates from a laser diode which is periodically modulated with time and at a continuous tone around an average output value.

13. An optical pH sensor as set forth in claim 10 wherein said output fibers each have diameters larger than said input fiber.

14. A method as set forth in claim 1 wherein said transparent window is constructed of sapphire.

15. A method as set forth in claim 8 wherein said step of servicing said sensor head further comprises the steps of:
removing said sensor head from said fluid;
cleaning and/or reapplying said thin protein layer;
verifying said sensor head fouling is no longer occurring; and
returning said sensor head into said fluid.

16. An optical pH sensor as set forth in claim 10 wherein said transparent window is constructed of sapphire.

* * * * *